United States Patent
Bhuiya et al.

(10) Patent No.: US 10,978,203 B2
(45) Date of Patent: Apr. 13, 2021

(54) POWER-EFFICIENT HEALTH AFFLICTION CLASSIFICATION

(71) Applicant: INTERNATIONAL BUSINESS MACHINES CORPORATION, Armonk, NY (US)

(72) Inventors: Subhajit Bhuiya, Bangalore (IN); Vijay Ekambaram, Tamilnadu (IN); Ramasuri Narayanam, Bangalore (IN); Ashwin M. Narvekar, Bangalore (IN)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 354 days.

(21) Appl. No.: 15/627,801

(22) Filed: Jun. 20, 2017

(65) Prior Publication Data
US 2018/0365382 A1 Dec. 20, 2018

(51) Int. Cl.
*G16H 40/63* (2018.01)
*G06F 19/00* (2018.01)
(Continued)

(52) U.S. Cl.
CPC ............. *G16H 40/63* (2018.01); *G06F 1/163* (2013.01); *G06F 19/3456* (2013.01);
(Continued)

(58) Field of Classification Search
CPC .... G16H 50/30; G16H 40/63; G06F 19/3456; G06F 1/163
See application file for complete search history.

(56) References Cited

U.S. PATENT DOCUMENTS

| 3,651,694 A | 3/1972 | Lamb |
| 5,035,247 A | 7/1991 | Heimann |

(Continued)

FOREIGN PATENT DOCUMENTS

| WO | WO-2011160333 A1 * | 12/2011 | ............. G06F 9/445 |
| WO | 2012164482 A1 | 12/2012 | |

(Continued)

OTHER PUBLICATIONS

Roth, Erica, "The Best Heart Disease iPhone and Android Apps of the Year" [retrieved from the Internet on Apr. 19, 2017]. Retrieved from Internet URL: <http://www.healthline.com/health/heart-disease/top-iphone-android-apps#2>, 8 pgs.
(Continued)

*Primary Examiner* — Janice A Mooneyham
*Assistant Examiner* — Steven G Sanghera
(74) *Attorney, Agent, or Firm* — Michael O'Keefe; Matthew M. Hulihan; Heslin Rothenberg Farley & Mesiti PC (57) ABSTRACT

Power-efficient health affliction classification. A method controls execution of a set of health affliction classification applications on a wearable device of a user. The controlling includes monitoring device notifications on at least one mobile device of the user for health affliction information. The controlling further includes invoking an analysis of one or more notifications of the monitored device notifications, the analysis attempting to ascertain a health affliction and an afflicted individual having the health affliction. Based on the analyzing being initially unable to ascertain a health affliction, the controlling initiates execution of the set of health affliction classification applications in a prioritized order of execution.

17 Claims, 6 Drawing Sheets

(51) Int. Cl.
*G06F 1/16* (2006.01)
*G16H 50/30* (2018.01)
*G16H 40/20* (2018.01)
*G16H 20/10* (2018.01)
*G16H 40/67* (2018.01)

(52) U.S. Cl.
CPC ............. *G16H 20/10* (2018.01); *G16H 40/20* (2018.01); *G16H 40/67* (2018.01); *G16H 50/30* (2018.01)

(56) References Cited

U.S. PATENT DOCUMENTS

| | | | |
|---|---|---|---|
| 5,109,863 | A | 5/1992 | Semmlow et al. |
| 5,301,679 | A | 4/1994 | Taylor |
| 6,081,734 | A * | 6/2000 | Batz .................. A61B 5/14532 600/314 |
| 7,357,913 | B2 | 4/2008 | Hellerstein |
| 8,366,005 | B2 * | 2/2013 | Kotlarsky .......... G06K 7/10732 235/462.24 |
| 8,633,890 | B2 | 1/2014 | Tossell et al. |
| 8,862,448 | B2 | 10/2014 | Holmes et al. |
| 9,202,193 | B2 | 12/2015 | Kwak |
| 9,292,600 | B2 * | 3/2016 | Midgen ................ G06Q 10/107 |
| 9,612,883 | B2 * | 4/2017 | Dean ..................... G06F 9/4881 |
| 2009/0076350 | A1 | 3/2009 | Bly et al. |
| 2010/0161345 | A1 * | 6/2010 | Cain ...................... G06Q 10/08 705/2 |
| 2012/0245439 | A1 | 9/2012 | Andre et al. |
| 2013/0261771 | A1 | 10/2013 | Ten Kate |
| 2014/0087758 | A1 * | 3/2014 | Maor .................... G01S 5/0252 455/456.1 |
| 2014/0378777 | A1 | 12/2014 | Conrad et al. |
| 2016/0117202 | A1 * | 4/2016 | Zamer .................... H04L 67/26 719/320 |
| 2016/0142407 | A1 * | 5/2016 | Chun .................. H04L 63/0861 726/5 |
| 2016/0284038 | A1 * | 9/2016 | Johnson ............... G06Q 50/265 |
| 2018/0113987 | A1 * | 4/2018 | Zhu ........................ G16H 50/20 |

FOREIGN PATENT DOCUMENTS

| | | |
|---|---|---|
| WO | 2014122467 A1 | 8/2014 |
| WO | 2015056239 A1 | 4/2015 |
| WO | 2015079436 A1 | 6/2015 |
| WO | 2015127142 A1 | 8/2015 |

OTHER PUBLICATIONS

"Top Android Apps for Your Heart" written Nov. 8, 2013, [retrieved from the Internet on Apr. 19, 2017]. Retrieved from Internet URL: <http://www.droidreport.com/top-android-apps-your-heart-2060>, 2 pgs.

Longstaff, Brent, "Improving Activity Classification for Health Applications on Mobile Devices using Active and Semi-Supervised Learning" [retrieved from the Internet on Apr. 19, 2017]. Retrieved from Internet URL: <http://www.cs.cornell.edu/~destrin/resources/conferences/2010-mar-Longstaff.pdf>, 7 pgs.

Azumio, https://www.azumio.com/, 4 pages (last accessed Apr. 20, 2017).

Surangsrirat, Decho, "Android application for spiral analysis in Parkinson's Disease" [retrieved from the Internet on Apr. 19, 2017]. Retrieved from Internet URL: <https://www.researchgate.net/publication/254032328_Android_application_for_spiral_analysis_in_Parkinson's_Disease>, IEEE, Mar. 2012, 16 pgs.

Griffiths, Sarah, "Could we soon diagnose autism using Hand Movements? Unique tics and actions could be used to identify mental health conditions" [retrieved from the Internet on Apr. 19, 2017]. Retrieved from Internet URL: <http://www.dailymail.co.uk/sciencetech/article-3504776/Could-soon-diagnose-autism-using-HAND-MOVEMENTS-Unique-ticks-actions-used-identify-mental-health-conditions.html>, Pub Mar. 22, 2016; Updated Mar. 23, 2016, 5 pgs.

"White Eye Detector App Released for Android Devices" [retrieved from the Internet on Apr. 19, 2017]. Retrieved from Internet URL: <http://knowtheglow.org/white-eye-detector-app-released-for-android-devices/>, posted Sep. 15, 2015, © 2017 Know The Glow, 3 pgs.

Siddique, Ashik, "Biosensor Smartphone App Is a Cheap Disease-Detecting Spectrometer" [VIDEO] [retrieved from the Internet on Apr. 19, 2017]. Retrieved from Internet URL: <http://www.medicaldaily.com/biosensor-smartphone-app-cheap-disease-detecting-spectrometer-video-246187>, May 23, 2013, 8 pgs.

"Dermatology Apps" [retrieved from the Internet on Apr. 19, 2017]. Retrieved from Internet URL: <http://internetmedicine.com/dermatology-apps/>, © 2016 Internet Medicine Digital Healthcare, 3 pgs.

"Prototype Early Warning System" [retrieved from the Internet on Apr. 19, 2017]. Retrieved from Internet URL: <http://www.ncbi.nlm.nih.gov/pubmed/25570737>, Conf Proc IEEE Eng Med Biol Soc. 2014;2014:3468-71. doi: 10.1109/EMBC.2014.6944369, 2 pgs.

"Pocket diagnosis: App turns any smartphone into a portable medical diagnostic device" [retrieved from the Internet on Apr. 19, 2017]. Retrieved from Internet URL: <https://www.sciencedaily.com/releases/2014/03/140319103612.htm>, Mar. 19, 2014, 4 pgs.

Putthaprasart, Taksa-on, "Medicine Intake Detection Using a Wearable Wrist Device Accelerometer", 2012 4th International Conference on Computer Engineering and Technology (ICCET 2012), IPCSIT vol. 40 (2012) © (2012), IACSIT Press, Singapore, 5 pgs.

Wang, He, "MoLe: Motion Leaks through Smartwatch Sensors" [retrieved from the Internet on Apr. 19, 2017]. Retrieved from Internet URL: <http://synrg.csl.illinois.edu/papers/mole.pdf>, © 2015 ACM, 12 pgs.

PulsePoint, http://www.pulsepoint.org, 6 pages (last accessed Apr. 20, 2017).

Mell, Peter, et al., "The NIST Definition of Cloud Computing", NIST Special Publication 800-145, Sep. 2011, Gaithersburg, MD, 7 pgs.

* cited by examiner

POWER-EFFICIENT HEALTH AFFLICTION CLASSIFICATION

BACKGROUND

Mobile devices, such as smartphones, tablets, and wearable mobile devices ("wearables") have limited battery life and therefore must behave in a power-efficient manner. Wearable devices are especially susceptible to battery power depletion because they tend to be smaller devices with much smaller batteries than other types of mobile devices. Smartwatches, an example type of wearable device with limited battery life, are computerized wrist-watches that can run/execute mobile apps and collect motion sensor data, among other activities. However, it becomes increasingly difficult to leverage smartwatches and other wearables to their full potential when hindered by inefficient approaches to app execution and battery consumption resulting therefrom.

SUMMARY

Shortcomings of the prior art are overcome and additional advantages are provided through the provision of a computer-implemented method. The method controls execution of a set of health affliction classification applications on a wearable device of a user. The controlling includes monitoring device notifications on at least one mobile device of the user for health affliction information. The controlling further includes invoking an analysis of one or more notifications of the monitored device notifications, the analysis attempting to ascertain a health affliction and an afflicted individual having the health affliction. Based on the analyzing being initially unable to ascertain a health affliction, the controlling initiates execution of the set of health affliction classification applications in a prioritized order of execution.

Further, a computer program product including a computer readable storage medium readable by a processor and storing instructions for execution by the processor is provided for performing a method. The method controls execution of a set of health affliction classification applications on a wearable device of a user. The controlling includes monitoring device notifications on at least one mobile device of the user for health affliction information. The controlling further includes invoking an analysis of one or more notifications of the monitored device notifications, the analysis attempting to ascertain a health affliction and an afflicted individual having the health affliction. Based on the analyzing being initially unable to ascertain a health affliction, the controlling initiates execution of the set of health affliction classification applications in a prioritized order of execution.

Yet further, a computer system is provided that includes a memory and a processor in communications with the memory, wherein the computer system is configured to perform a method. The method controls execution of a set of health affliction classification applications on a wearable device of a user. The controlling includes monitoring device notifications on at least one mobile device of the user for health affliction information. The controlling further includes invoking an analysis of one or more notifications of the monitored device notifications, the analysis attempting to ascertain a health affliction and an afflicted individual having the health affliction. Based on the analyzing being initially unable to ascertain a health affliction, the controlling initiates execution of the set of health affliction classification applications in a prioritized order of execution.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

As noted, a smartwatch is an example type of wearable mobile device, also referred to as a "wearable", that is a computerized wrist-watch that runs/executes mobile applications ("apps") and collects motion sensor data, among other tasks. Other types of wearables include fitness and activity trackers, and head-mounted wearable devices ("smart glasses"), among many others. Examples are described herein with reference to smartwatches, though it is understood that concepts presented herein are applicable to other forms of wearable devices, mobile devices, or computer systems generally.

Smartwatches have limited battery life, making it difficult to run applications, especially power-hungry applications, on the smartwatch for an extended period of time. Meanwhile, smartwatches may be used in healthcare analytics because they have the capability to monitor health conditions like heartrate, blood pressure, body mass index, stress levels, physical activity, and the like. Smartwatches also tend to include built-in motion sensors like accelerometers, gyroscopes, pedometers, etc. that capture movement and gesture information e.g. hand movements.

Different diseases, medical conditions, and the like (referred to herein collectively as "health afflictions") have associated therewith different patterns of human behavior. If an individual has a cough and runny nose, that individual will typically move his or her hand toward the individual's mouth and nose very frequently, i.e. relative to individuals who do not suffer from those afflictions. Similarly, when an individual has a cold, the individual sneezes and moves his or her hands toward the individual's mouth potentially several times in a short timeframe.

Dedicated algorithms can be developed to detect various human-body behavior patterns, in order to identify or 'classify' the health affliction(s) afflicting the individual to thereby identify a disease or condition the user is experiencing. So called classifier or classification applications, can be installed on a smartwatch to provide disease detection. The smartwatch can capture, using the built-in motion sensors, data describing human hand movement. The affliction might have unique hand movement behavior related to sniffling, coughing, taking medicine, etc. Various classifier algorithms can thus be applied against the hand movement data to determine the health affliction afflicting the user.

Running one or more classification apps on the smartwatch can be very power consuming. Many classification apps may be configured expecting to run constantly as a background process of the smartwatch, continually consuming power. This presents a challenge given that the smartwatch has limited battery power that should be used efficiently.

Thus, there are conflicting goals in the desire for robust classification apps to run locally on the smartwatch (or other wearable), while conserving batter power to the extent possible. Regarding the desire for the classification app to run locally on the smartwatch, it is possible to offload the classification assessment. The wearable could periodically send hand movement and other motion information to a remote device that can run the health affliction classification app(s) in an attempt to detect the health affliction, thereby minimizing power consumption of the smartwatch. However, there are privacy concerns when offloading data to a remote server. Motion sensor data could include sensitive data informing of, as an example, keystroke patterns, which could be used to retrieve user passwords. Hence, there are security concerns when offloading motion sensor and other kinds of data.

Running all of the classification apps locally, while potentially more secure, could lead to heavy power drain as noted. Furthermore, it may be unnecessary to constantly run one or many classification apps on the wearable of a person who is generally very healthy.

Described herein are aspects for intelligently triggering health affliction classification apps in a power and privacy-aware way to automatically detect user health afflictions. Classification can be important because once an affliction is classified, various operations can be triggered, for instance sending notifications to close friends and family informing that the user is ill, sending notifications to the user's physician for medical advice, retrieving contact information of a nearby doctor who can treat the affliction, and sending proactive actions to the user based on the affliction. Additionally, using location of an individual assessed to be afflicted with a given health affliction, a system can ascertain a viral hot-spot and provide to others warnings regarding the area or preventative measures.

Figure 1:
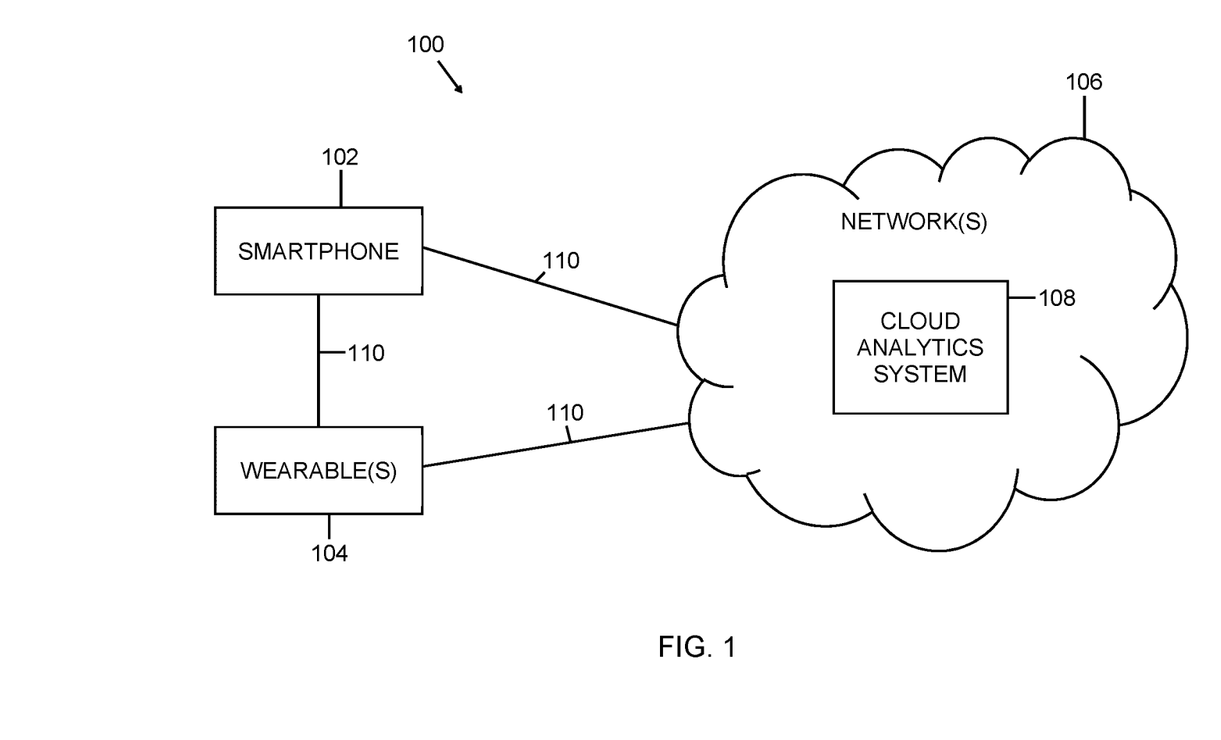
FIG. 1 depicts an example environment to incorporate and/or use aspects described herein.

FIG. 1 depicts an example environment to incorporate and/or use aspects described herein. Environment 100 includes mobile devices of a user, e.g. a smartphone mobile device 102 of the user, the smartphone in communication with one or more wearable mobile devices ("wearables") 104 of the user. The communication is in one example a direct wireless connection, for instance a Bluetooth® wireless connection (BLUETOOTH is a registered trademark of Bluetooth SIG, Inc., Kirkland, Wash., U.S.A.). Smartphone 102 is in communication with network(s) 106, which may include any one or more networks, such as one or more local area networks and/or one or more wide area networks, such as the internet, and components hosted thereon. In this example, wearable(s) 104 are also in communication directly with network(s) 106, though in other examples they may not have a separate connection to network(s) 106 and instead may access the network(s) 106 via the paired smartphone. Devices 102, 104 may be in communication with network(s) 106 via wired or wireless communications links, such as wired and/or cellular, Wi-Fi, or other types of wireless connections. Hosted, for instance a cloud facility on the network, is a cloud analytics system 108 remote from the mobile devices of the user. The components in FIG. 1 form wired or wireless network(s), and communication between the devices takes place via wired or wireless communications links 114 for communicating data between the devices. FIG. 1 is just one example of an environment to incorporate and use aspects described herein.

In some aspects, wearable device(s), a user's smartphone, tablet, or other mobile device, and mobile device application(s) installed on one or more of the mobile device(s) are leveraged to analyze device notifications to ascertain health afflictions of individuals, potentially invoking execution of health affliction classification applications installed on wearable or other mobile device(s) of users to identify specific health afflictions affecting particular users. While examples provided herein involve wearable and other mobile devices, other types of computer systems may be utilized, for instance laptops, personal computers, and the like. Typically, wearables and other mobile devices incorporate sensors that can be leveraged as described herein, while laptops and desktop machines typically do not include these components, though there is no reason they could not, if desired. However, in some aspects, processing described herein that utilizes sensor or other measurement data to, for instance, analyze device notifications or perform other aspects described herein, may run on such non-mobile devices like a user's desktop computer if desired.

Figure 2:
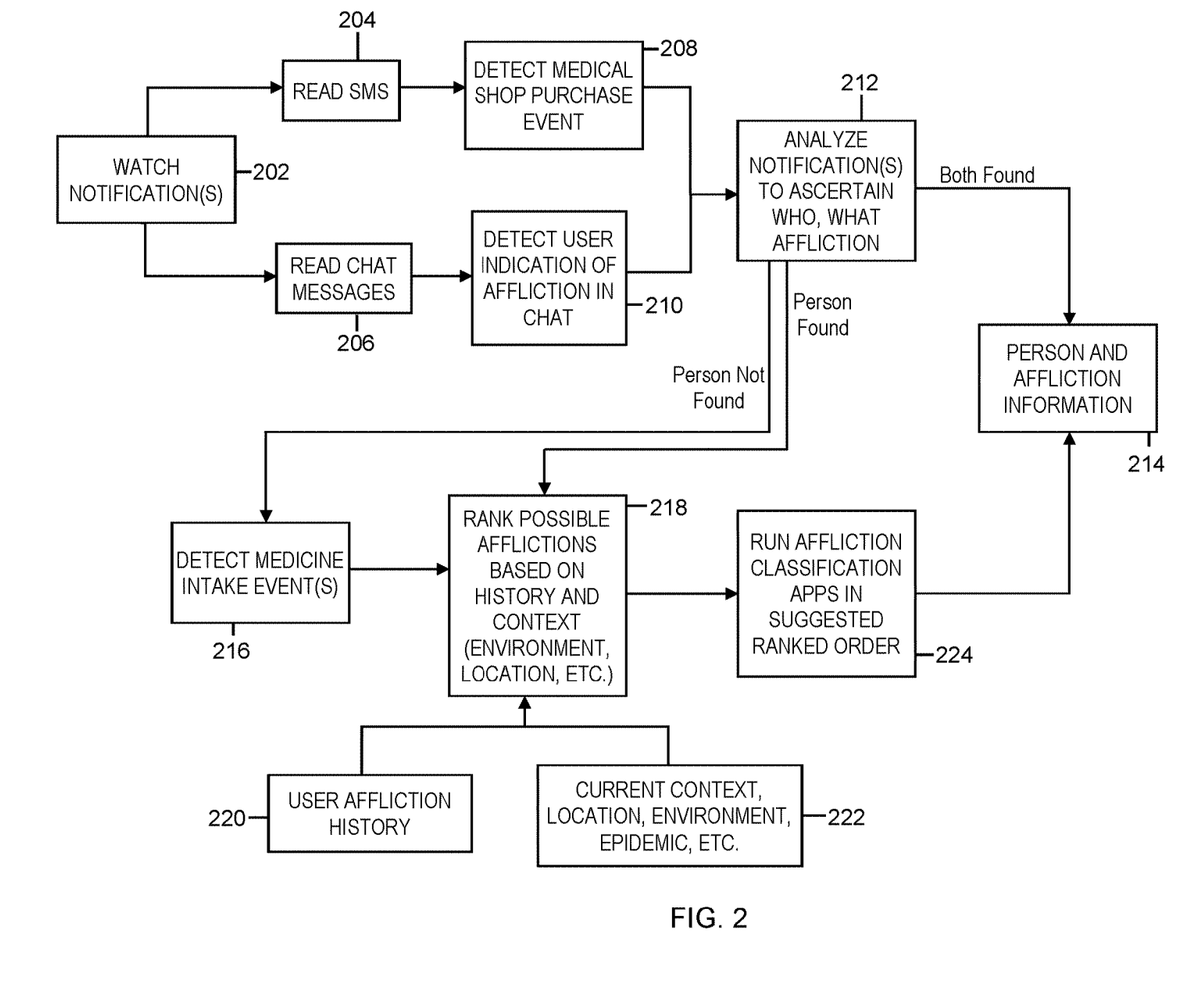
FIG. 2 depicts an example conceptual flow diagram of aspects described herein.

FIG. 2 depicts an example conceptual flow diagram of aspects described herein. Aspects of FIG. 2 may be performed by one or more computer systems, including but not limited to user mobile devices and/or remote systems such as an analytics server.

The flow begins with device notification analysis, which can monitor notifications on the user's smartwatch and/or smartphone or other mobile device, as examples. In this regard, there may be different types of smartwatches in terms of how notifications are received—some smartwatches receive notifications as a function of notifications received on a paired device, such as a smartphone to which the watch is paired. Other watches receive notifications directly from the internet or through a paired mobile device that does not also treat the notification event as a received notification for the mobile device. In any case, software running on the smartwatch, smartphone, or a combination, monitors device notifications on the respective device. Smart watches can have different types of notifications for different services, software, or capabilities, for instance SMS, social network messages, chat programs, email, and so on. Thus, the flow includes, on the basis of receiving notification(s) (202) on the smartwatch in this example, reading SMS message(s) (204) and chat message(s) (206), for instance those contained in the notifications themselves and/or in conversations to which those SMS/chat message(s) belong (extended notifications sometimes include some or all of a conversation right in the notification). At an initial stage of notification analysis, it can check for any information relating to or indicative of a potential health affliction, for instance a medical shop or pharmacy purchase (208) indicated by a received SMS notification. Examples include a text message indicating a recent purchase and/or information about a prescription, as examples. The significance of this information may be that the user or someone close to the user (family, friend, patient, etc.) is ill. In another example as shown in FIG. 2, the process can detect an indication of an affliction in a chat message (210), for instance when the user sends a message saying, "I am not well", "Suffering from a cough", or the like, indicating that the user or someone close to the user is may be ill. In another example, the user may send a leave of absence or set an out of-office email because of an affliction.

This notification monitoring and analysis may be performed by any of various methods. As an example, a process or other software can run in the background of the device and have administrator or other privileges to intercept or at least monitor events that are triggered by notification receipt. A lightweight app that consumes very little power may continually run in this manner, and may or may not be part of the operating system of the device.

The flow proceeds by analyzing the notification(s) to ascertain the afflicted individual(s) and the particular affliction (212). In some aspects, the above monitoring/analyzing is a first level analysis to obtain affliction-related information, and this analysis (212) is a second-level textual analysis on that information to discover who is afflicted and what that affliction is.

If both the person and the affliction are ascertained by this analysis, the flow proceeds by providing desired information, such as information about the individual and the affliction (214). In one example, this information is provided to a remote server along with location information of the individual so the server becomes aware of where, geographically, the affliction is expressed. In this regard, there is no need for any additional processing by classification application(s)—none need to be triggered because the notification analysis has informed of the affliction and the individual. This saves power that would otherwise have been consumed by additional or continual classification software processing.

In some examples, the affliction and indication of the individual may be logged in application data of classification app(s) even when those app(s) are not running. This may be particularly useful in situations where classification apps on the smartwatch or other mobile device have been actively prevented from running (or paused), e.g. by software operating according to aspects described herein, on the basis that they are to be triggered subsequently, if needed, as described below. Some classification apps that are normally configured to execute continually may log data continually or periodically and expect this logged data to include accurate updated information when the classification app is triggered to run. If desired, some data could be logged for the application in its application data as part of this flow, without having to run the app itself.

The analysis at 212 may not identify the afflicted individual, although it has been determined that someone is afflicted with some affliction. The flow proceeds to 216 where it detects medicine intake event(s). The detection of medicine intake is performed because it is being assumed that the afflicted individual may take medicine or some other remedy. Known approaches are available that detect whether a user is taking medicine or other remedies, and are usually based on sensor-based detection of movement that matches the action of a user consuming pills, medicine, or other remedies. As an alternative to detecting medicine intake events, the process could detect—perhaps leveraging sensor data from the smartwatch—any actions that tend to indicate that a given user is afflicted with a health affliction.

In an enhancement, assuming medicine intake detection confirms that a given user is afflicted, this can trigger the running of medicine intake classification app(s) or similar software in mobile devices of related users, such as family member or friends, and optionally for a predefined time frame, in an effort to identify multiple related individuals who may be afflicted with a contagious or common affliction.

After detecting medicine intake event(s) and identifying the afflicted individual, or if instead at 212 the individual was ascertained, the flow proceeds to detect what the affliction is, if not already known. In this example, it ranks possible afflictions (218) based on, e.g. user history 220 and contextual information (222) such as location, environment, the presence of local or regional epidemics, etc. In the event that more data is needed to identify possible afflictions, the flow can pause, awaiting more data, and/or return to an earlier aspect, for instance 202.

The ranking may be performed by the smartwatch, companion mobile device (e.g. paired smartphone) and/or a remote server, such as an analytics server that receives some data from the smartwatch and applies analytics to identify candidate or likely afflictions, for instance based on textual analysis of notification content.

With a ranked or prioritized list of possible afflictions, a corresponding set of health affliction classification apps can be triggered in a prioritized order of execution (224) until the particular health affliction that the user is suffering can be identified with a threshold degree of confidence. The health affliction detection processing may therefore be triggered in the smartwatch, i.e. by execution of classification app(s) on the smartwatch to classify the affliction. In this regard, the classification app(s) may examine/analyze data collected by the smartwatch but not shared to an external device such as a paired smartphone or remote server.

The classification apps may be initially stopped, paused or non-loaded. In some examples, software integrates with the device operating system to block these apps from running at startup. Software can then trigger execution of the apps as dictated by the prioritized order of execution to control their execution. The operating system could do this, or it could be done with a separate app with administrator privileges, for instance. In yet another embodiment, the classification apps are executed in a sandbox application with privileges to control execution of the classification apps It is also noted that aspects of FIG. 2 may be performed by software executing on a companion device to the smartwatch, for instance a paired smartphone, and that software may communicate with some software on the smartwatch to cause the execution of classification app(s) on the smartwatch.

A prioritized order of execution may be useful because it can run classification apps in a particular order (which may be determined dynamically as they are run) that is selected to more immediately assess the most likely afflictions, potentially saving time and power to classify the affliction. The prioritization can be based on location (of the device and by proxy the user), weather, season, user past disease history, local or regional epidemics, and so on. Different afflictions may exhibit themselves in different seasons and weather conditions. In the wintertime, the probability of the affliction being a cough or cold is greater than in the summertime. During a rainy season, the user may suffer from malaria. When there is an affliction epidemic or outbreak in a given area, a classification app to identify that affliction may be ranked higher for users in that area on the basis that they are at an increased risk than users in other areas not under the same outbreak.

In some examples, a central server, such as a cloud-based analytics platform considers all relevant factors to build and send to the smartwatch or smartphone a ranked list of classifiers/classification apps to run, optionally in serial order, on the user's smartwatch against data logged or to be logged by the wearable device. In some situations, the user may not have a classification app recommended by the analytics system. The wearable or another device of the user could automatically download and install the app in that case, or inform the user to install the app.

With, or as part of, the suggested ranked order, an indication of context (when, where, under which conditions, etc.) may also be indicated for running the classification apps. Classification may be most successful when the apps are run during specific timeframes, for instance while the user is sleeping, or while the user is awake, as examples.

The user's smartwatch/smartphone can reach out to the analytics system to provide the necessary information (if not already provided) for the system to rank the possible classifiers in the order in which they should be invoked to most efficiently identify the affliction. The information provided from the smartwatch or mobile device to the remote system can depend on what classifications are to be ranked, but emphases can include a lightweight amount, and periodic (rather than continuous) data stream. The minimum information needed is provided, in some cases, for instance content of notification(s) that was/were intercepted, any follow-up input received on the smartwatch, and an indication of the associated user(s) involved with the notification. Example information can also include properties of the medicine intake events that the smartwatch has recognized for the user. The analytics system provides a list, in some examples, that is sent back to the smartwatch.

Referring back to FIG. 2, the flow proceeds from 224, once the individual and the affliction have been identified, to 214 to provide information indicating the individual and the affliction. In some examples, the provided information is provided to the remote system, the user, and/or software of a device of the user, as examples.

Accordingly, provided is a power and privacy-aware method to start and stop the health affliction classification apps in wearable and other mobile devices. These may be stopped/started for contexts, for instance when it is highly probable to discover a given health affliction. Power savings is achieved through a trigger-based approach for applying increasingly more involved levels of analysis and execution when it makes sense to do so. For instance:

Trigger 1: Switch on smartwatch and auto-start Trigger 2;

Trigger 2: Basic notification analysis through simple keyword spotting; analyze keywords in notifications of the smartwatch to detect whether the user or family/friends are afflicted with a disease or other affliction. Repeat until positive indication, then when positive, start Trigger 3;

Trigger 3: Advanced notification analysis against user chats, messages, etc. and correlate with user's past affliction history to figure out the affliction and/or who is afflicted. If Trigger 3 figured out both, break; else if afflicted individual is not ascertained, proceed to Trigger 4; else (if afflicted individual is ascertained) proceed to Trigger 5;

Trigger 4: Medicine Intake classifier start: Start medicine intake classifier app on the smartwatch of user and others close to the user, to detect hand movement indicating intake of tablets or other medication/remedies. If Trigger 4 is positive for User X, then User X is tagged as the afflicted individual (individual having some affliction), and start Trigger 5 in User X's smartwatch or other wearable device;

Trigger 5: Rank the available classification apps installed on (or available to) User X's wearable device, e.g. based on user X location, context, medical history and other dynamic metadata, and start executing the classification apps in ranked order.

The above trigger sequence (Trigger 1->2->3->4->5) helps in starting and stopping the classification apps in the smartwatch at specific times in an effort to quickly identify an affliction and user with high probability and efficient power usage.

The execution of the classification apps that are ranked in order of priority can proceed serially (in terms of their sequential invocation of execution) and may optionally run at least somewhat concurrently. That is, it need not be the case that one classification app complete its assessment/execution before the next classification app is executed, though such behavior is a possibility. In some examples, the next classification app is triggered some configuration amount of time after its prior classification app.

Features described herein can optionally provide no motion sensor data to any outside device, e.g. away from the wearable device, helping to minimize privacy concerns. Meanwhile, a power consumption hierarchy and triggering scheme (Power(Trigger 5)>Power(Trigger 4)>Power(Trigger 3)>Power(Trigger 2)>Power(Trigger 1)) is setup to ensure that the highest power consuming activities (the execution of the classification applications) are undertaken only when it is efficient to do so and in an order to minimize the amount of time when a classification app is running.

By triggering Trigger n only after Trigger n−1 is positive, the system can remain in relatively lower power consumption states when the user and related users are relatively healthy. The system can move to other, relatively higher power states only when there are strong indications that an affliction is present.

Notification analysis may already be applied in smartwatches and mobile devices for various user personalizations and recommendations. In these cases, no, or minimal, additional power is being consumed by the first-level notification analysis described above.

Medicine intake detection may be triggered only after certain indicators are present that the user may have an affliction. Disease classification apps are triggered only after even further indicators that the user may have an affliction.

Accordingly, classification apps need not run continuously. Instead, approaches described herein trigger classification apps at times and in contexts when there are indicators that the user might be afflicted with particular affliction(s) that the apps are configured to identify. Keywords in notifications displayed on the wearable device are analyzed to detect whether the user and optionally related users may be afflicted. Medicine intake detection is started and utilized for the user and optionally related individuals, to detect, e.g., hand movement indicating intake of medicine in order to identify the afflicted individual(s). Additionally, aspects rank the available classification apps installed on the user's mobile device, which tanking may be based in part on the user's location, context, medical history, and other data, to prioritize and trigger execution of the classification apps in a prioritized order.

Figure 3:
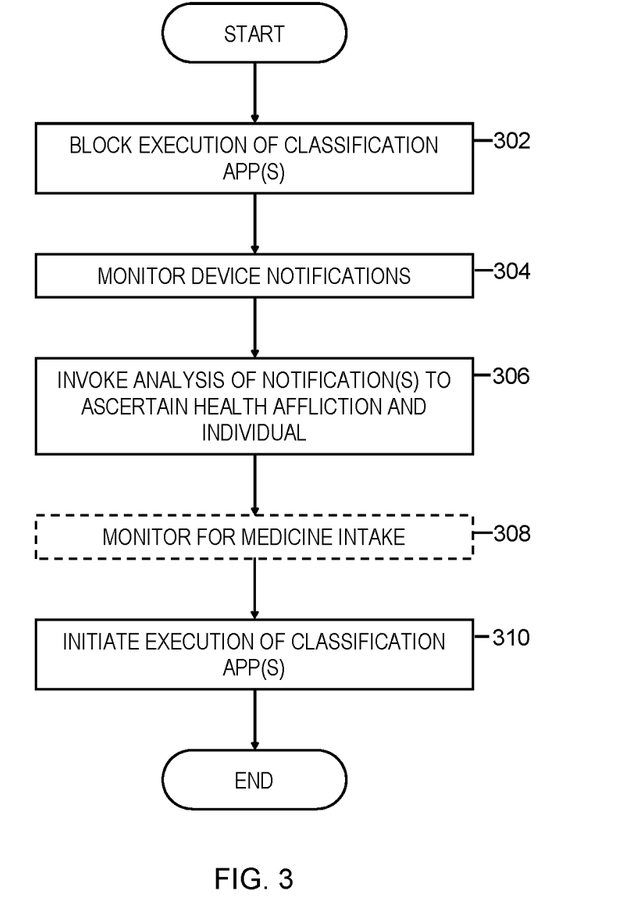
FIG. 3 depicts an example process for power-efficient health affliction classification, in accordance with aspects described herein.

FIG. 3 depicts an example process for in accordance with aspects described herein. In some examples, the process is performed by one or more computer systems, such as those described herein, which may include one or more mobile devices of a user or users, one or more cloud servers or systems, one of more other computer systems, or any combination of the foregoing.

The process may be performed as part of method of controlling execution of a set of health affliction classification applications on a wearable device of a user. The process includes initially blocking execution of the set of health affliction classification applications on the wearable device (302). In this manner, each of the health affliction classification application of the set of health affliction classification applications is idle unless execution thereof has been initiated as part of a prioritized order of execution. The blocking of the execution may be an explicit prevention of the apps from running (for instance blocking at startup or terminating the processes prematurely). It is noted that this blocking may not be necessary in cases where the classification app(s) are not configured to run at startup.

The process proceeds by monitoring device notifications on at least one mobile device of the user for health affliction information (304). The notifications could be notifications on any device of the user, for instance the user's smartphone paired to a wearable device, or the wearable device itself. Thus, the at least one mobile device can include a wearable device, where the monitored notifications include notifications of the wearable device, and wherein the wearable device is a smartwatch.

The monitoring can employ an initial level of analysis to examine each notification to identify whether it may be at all related to a health affliction. In some examples, the monitoring monitors for notifications of received messages (text, messenger, etc.) of at least one conversation of a messaging application (text messaging application, messenger application, email application, etc.).

The process then invokes an analysis of one or more notifications of the monitored device notifications (306). The analysis attempts to ascertain a health affliction and an afflicted individual having the health affliction. This may be a deeper notification analysis, in which notification(s) that are deemed pertinent can be more deeply analyzed, for instance by a remote analytical system, in an attempt to identify an affliction and afflicted person.

The afflicted individual may be the subject user, where the analysis includes correlating content of a monitored conversation to a health history of the user to ascertain the health affliction. In some examples, the analysis analyzes textual content of the conversation. Thus, in some examples, not only the portion of a conversation in a notification is analyzed, but so too are portions of the rest of the conversation, for instance as portions stored in the separate messaging application.

Based on the analyzing (306) being initially unable to ascertain an afflicted individual having the health affliction, the process proceeds to the aspect of monitoring for intake of medicine by the user (308). Medicine intake for other uses may also be monitored. In this regard, though not shown, some aspects can identify, based on content of the one or more notifications, one or more other users who may potentially be afflicted with the health affliction (for instance family members of the user, or other users with whom the user discusses being sick). The process could then initiate monitoring, by one or more other devices of the one or more other users, for intake of medicine by the one or more other users.

Based on the analyzing being initially unable to ascertain a health affliction, the process initiates execution of the set of health affliction classification applications in a prioritized order of execution (310). The initiating execution can initiate execution of one or more health affliction classification applications of the set of health affliction classification applications in-series until a health affliction is identified. Thus, the execution is initiated but it may be the case that only a single such classification application is actually executed, for instance if that application confidently classifies the affliction. It is also noted that the invoking may be done by the wearable device or by another device, such as a paired smartphone or remote system, as examples.

Based on identifying the health affliction, the process can log an indication of the health affliction on the mobile device, for instance in some application thereof.

In some embodiments where a remote system is leveraged, the process can include providing data of the at least one mobile device to a remote system, and receiving from the remote system, in return, an indication of the prioritized order of execution of the set of health affliction classification applications. The provided data can be any data that the wearable or other mobile device provides to the remote server in order for the remote server to properly prioritize the classification apps for execution. In some examples, the order of execution is prioritized based on location of the user, weather of the location of the user, time of year, and/or a medical history of the user.

Although various examples are provided, variations are possible without departing from a spirit of the claimed aspects.

Figure 4:
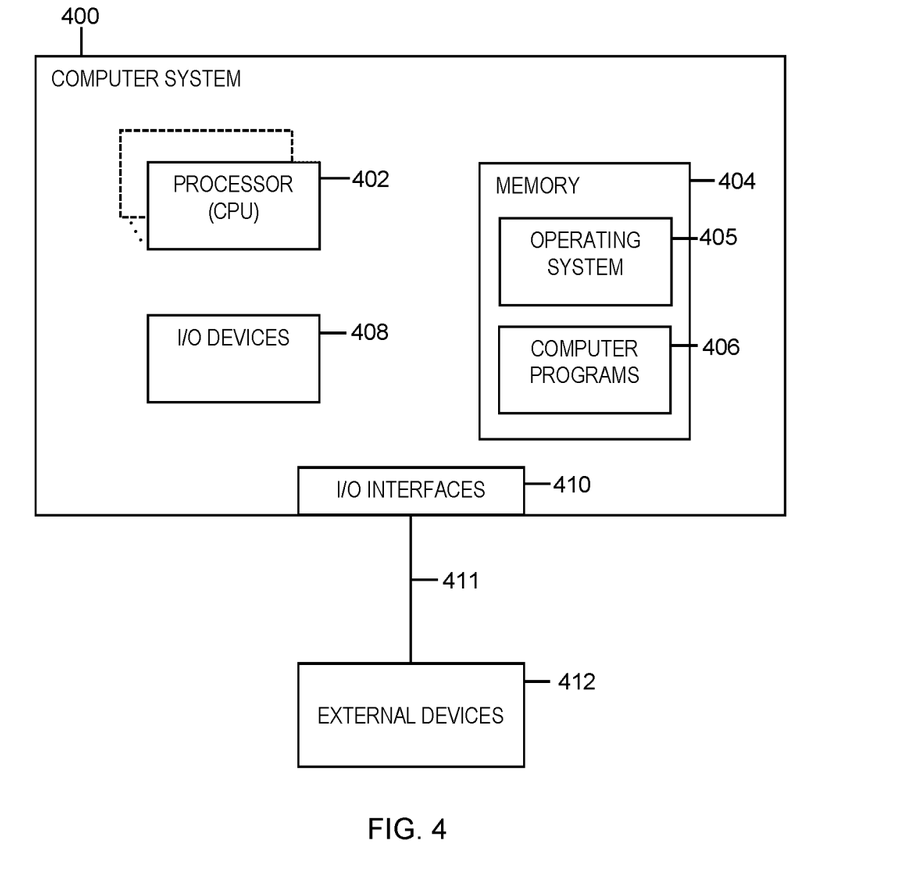
FIG. 4 depicts one example of a computer system and associated devices to incorporate and/or use aspects described herein.

Processes described herein may be performed singly or collectively by one or more computer systems, such as one or more mobile devices of a user or users, one or more cloud servers or systems, one of more other computer systems, or a combination of the foregoing, as examples. FIG. 4 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by International Business Machines Corporation (Armonk, N.Y., USA), Intel Corporation (Santa Clara, Calif., USA) or ARM Holdings plc (Cambridge, England, United Kingdom), as examples.

FIG. 4 shows a computer system 400 in communication with external device(s) 412. Computer system 400 includes one or more processor(s) 402, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 402 can also include register(s) to be used by one or more of the functional components. Computer system 400 also includes memory 404, input/output (I/O) devices 408, and I/O interfaces 410, which may be coupled to processor(s) 402 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 404 can be or include main or system memory (e.g. Random Access Memory) used in the execution of program instructions, storage device(s) such as hard drive(s), flash media, or optical media as examples, and/or cache memory, as examples. Memory 404 can include, for instance, a cache, such as a shared cache, which may be coupled to local caches (examples include L1 cache, L2 cache, etc.) of processor(s) 402. Additionally, memory 404 may be or include at least one computer program product having a set (e.g., at least one) of program modules, instructions, code or the like that is/are configured to carry out functions of embodiments described herein when executed by one or more processors.

Memory 404 can store an operating system 405 and other computer programs 406, such as one or more computer programs/applications that execute to perform aspects described herein. Specifically, programs/applications can include computer readable program instructions that may be configured to carry out functions of embodiments of aspects described herein.

Examples of I/O devices 408 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device may be incorporated into the computer system as shown, though in some embodiments an I/O device may be regarded as an external device (412) coupled to the computer system through one or more I/O interfaces 410.

Computer system 400 may communicate with one or more external devices 412 via one or more I/O interfaces 410. Example external devices include a keyboard, a pointing device, a display, and/or any other devices that enable a user to interact with computer system 400. Other example external devices include any device that enables computer system 400 to communicate with one or more other computing systems or peripheral devices such as a printer. A network interface/adapter is an example I/O interface that enables computer system 400 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Wash., U.S.A.).

The communication between I/O interfaces 410 and external devices 412 can occur across wired and/or wireless communications link(s) 411, such as Ethernet-based wired or wireless connections. Example wireless connections include cellular, Wi-Fi, Bluetooth®, proximity-based, near-field, or other types of wireless connections. More generally, communications link(s) 411 may be any appropriate wireless and/or wired communication link(s) for communicating data.

Particular external device(s) 412 may include one or more data storage devices, which may store one or more programs, one or more computer readable program instructions, and/or data, etc. Computer system 400 may include and/or be coupled to and in communication with (e.g. as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 400 may be operational with numerous other general purpose or special purpose computing system environments or configurations. Computer system 400 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

Aspects described herein may be incorporated into and/or use a cloud computing environment. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for loadbalancing between clouds).

A cloud computing environment is service oriented with a focus on statelessness, low coupling, modularity, and semantic interoperability. At the heart of cloud computing is an infrastructure comprising a network of interconnected nodes. One such node is node 10 depicted in FIG. 5.

Figure 5:
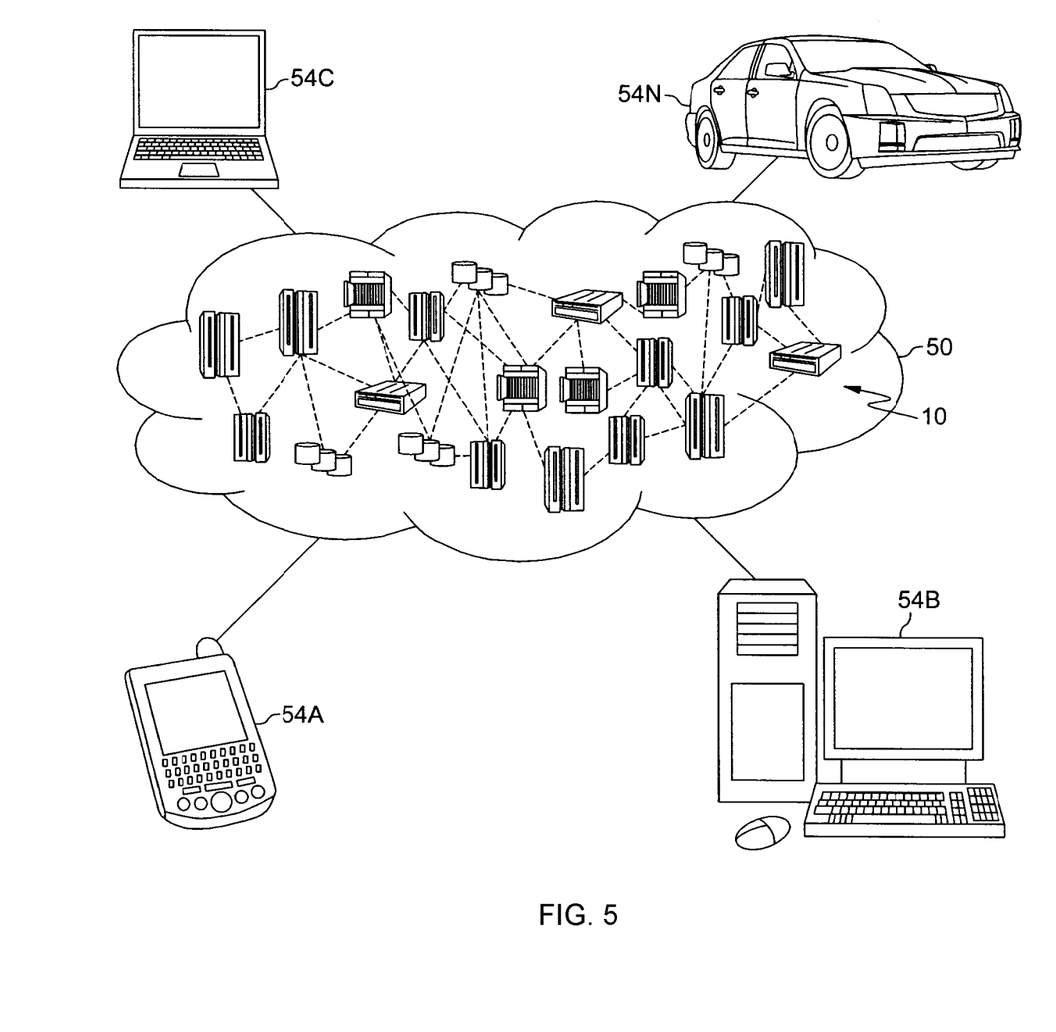
FIG. 5 depicts a cloud computing environment according to an embodiment of the present invention.

Computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

Referring now to FIG. 5, illustrative cloud computing environment 50 is depicted. As shown, cloud computing environment 50 comprises one or more computing nodes 10 with which local computing devices used by cloud consumers, such as, for example, smartphone or other mobile device 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
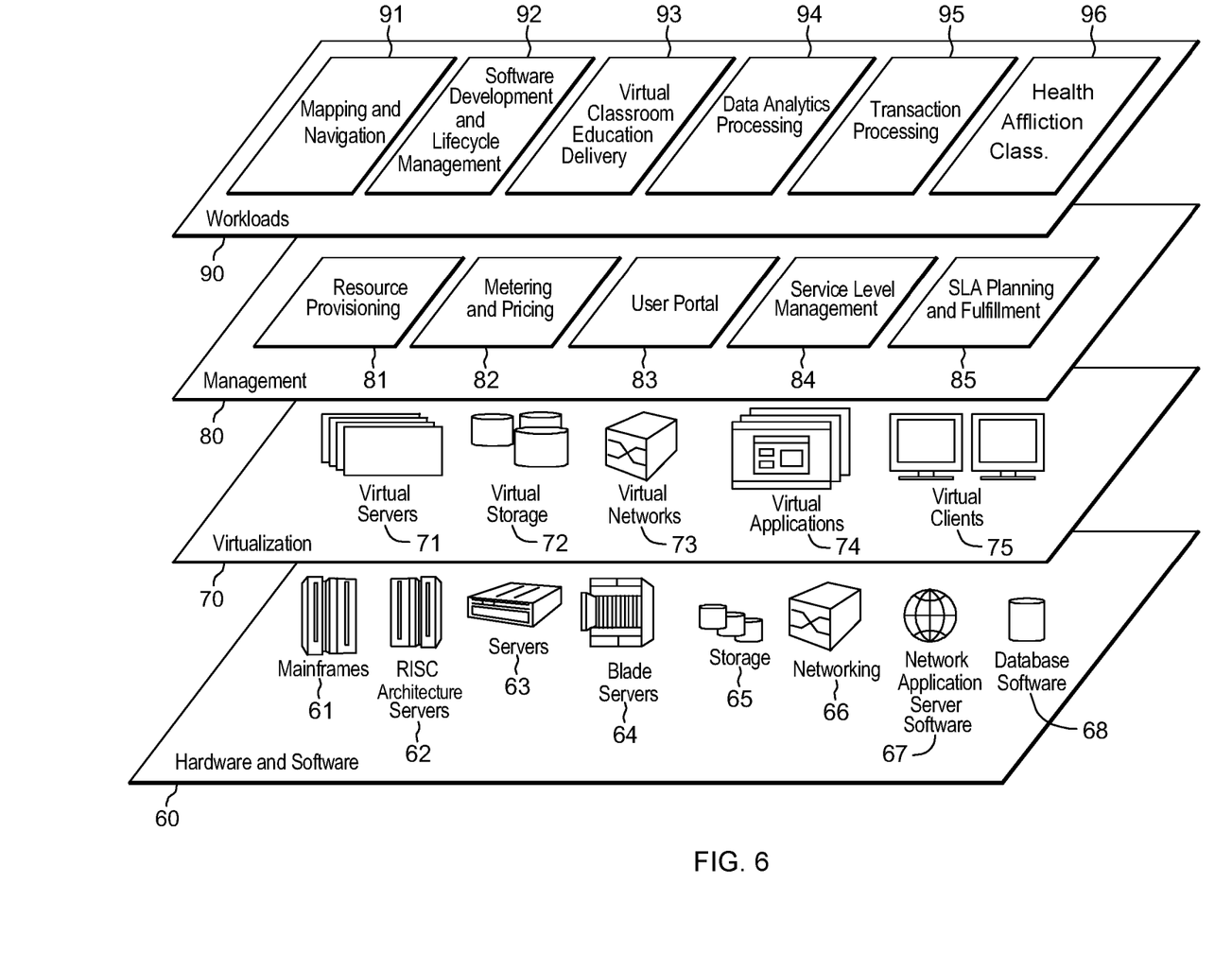
FIG. 6 depicts abstraction model layers according to an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and health affliction classification 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method comprising:
controlling power consumption of a wearable device of a user by selectively starting and stopping, automatically by a processing circuit, execution of a set of health affliction classification applications on the wearable device of the user, the controlling comprising:
monitoring device notifications on at least one mobile device of the user for health affliction information, wherein the monitoring monitors notifications corresponding to various different electronic communication services, including text and e-mail messaging services, and wherein the monitoring is performed at least in part as the set of health affliction classification applications on the wearable device are idle;
invoking an analysis of one or more notifications of the monitored device notifications, the analysis comprising checking the monitored notifications for textual content informing of potential health afflictions and attempting to ascertain a health affliction and an afflicted individual having the health affliction; and
initiating execution of the set of health affliction classification applications on the wearable device in a prioritized order of execution, based on the analyzing being initially unable to ascertain a health affliction after attempting to ascertain the health affliction;
wherein the initiating execution initiates execution of one or more health affliction classification applications of the set of health affliction classification applications in-series until a health affliction is identified, wherein, based on initiating execution of a health affliction classification application of the one or more health affliction classification applications, an attempt is made to identify the health affliction prior to initiating execution of a sequentially-next health affliction classification application of the one or more health affliction classification applications, wherein based on identifying the health affliction after initiating execution of a health affliction classification application, the initiating execution avoids initiating execution of any sequentially-next health affliction classification application of the one or more health affliction classification applications, and wherein the method further comprises logging an indication of the health affliction on the mobile device.

2. The method of claim 1, wherein the monitoring monitors for notifications of received messages of at least one conversation of a messaging application, and wherein the analysis analyzes textual content of the at least one conversation.

3. The method of claim 2, wherein the afflicted individual is the user, and wherein the analysis comprises correlating content of the at least one conversation to a health history of the user to ascertain the health affliction.

4. The method of claim 1, further comprising, based on the analyzing being initially unable to ascertain an afflicted individual having the health affliction, monitoring for intake of medicine by the user.

5. The method of claim 4, wherein the controlling further comprises:
identifying, based on content of the one or more notifications, one or more other users who may potentially be afflicted with the health affliction; and
initiating monitoring, by one or more other devices of the one or more other users, for intake of medicine by the one or more other users.

6. The method of claim 1, wherein the controlling further comprises:
providing data of the at least one mobile device to a remote system; and
receiving from the remote system an indication of the prioritized order of execution of the set of health affliction classification applications.

7. The method of claim 1, wherein the order of execution is prioritized based on at least one selected from the group consisting of: location of the user, weather of the location of the user, time of year, and a medical history of the user.

8. The method of claim 1, wherein the selectively starting and stopping execution of the set of health affliction classification applications comprises blocking the set of health affliction classification applications from execution on startup of the wearable device, wherein each health affliction classification application of the set of health affliction classification applications remains idle unless and until execution thereof is initiated as part of the prioritized order of execution.

9. The method of claim 1, wherein the at least one mobile device comprises the wearable device, wherein the monitored notifications comprise notifications of the wearable device, and wherein the wearable device is a smart watch.

10. A computer system comprising:
a memory; and
a processor in communication with the memory, wherein the computer system is configured to perform a method comprising:
controlling power consumption of a wearable device of a user by selectively starting and stopping, automatically by a processing circuit, execution of a set of health affliction classification applications on the wearable device of the user, the controlling comprising:
monitoring device notifications on at least one mobile device of the user for health affliction information, wherein the monitoring monitors notifications corresponding to various different electronic communication services, including text and e-mail messaging services, and wherein the monitoring is performed at least in part as the set of health affliction classification applications on the wearable device are idle;
invoking an analysis of one or more notifications of the monitored device notifications, the analysis comprising checking the monitored notifications for textual content informing of potential health afflictions and attempting to ascertain a health affliction and an afflicted individual having the health affliction; and
initiating execution of the set of health affliction classification applications on the wearable device in a prioritized order of execution, based on the analyzing being initially unable to ascertain a health affliction after attempting to ascertain the health affliction;
wherein the initiating execution initiates execution of one or more health affliction classification applications of the set of health affliction classification applications in-series until a health affliction is identified, wherein, based on initiating execution of a health affliction classification applications, an attempt is made to identify the health affliction prior to initiating execution of a sequentially-next health affliction classification application of the one or more health affliction classification applications, wherein based on identifying the health affliction after initiating executing of a health affliction classification application, the initiating execution avoids initiating executing of any sequentially-next health affliction classification application of the one or more health affliction classification applications, and wherein the method further comprises logging an indication of the health affliction on the mobile device.

11. The computer system of claim 10, wherein the method further comprises:
based on the analyzing being initially unable to ascertain an afflicted individual having the health affliction, monitoring for intake of medicine by the user;
identifying, based on content of the one or more notifications, one or more other users who may potentially be afflicted with the health affliction; and
initiating monitoring, by one or more other devices of the one or more other users, for intake of medicine by the one or more other users.

12. The computer system of claim 10, wherein the order of execution is prioritized based on at least one selected from the group consisting of: location of the user, weather of the location of the user, time of year, and a medical history of the user.

13. The computer system of claim 10, wherein the selectively starting and stopping execution of the set of health affliction classification applications comprises blocking the set of health affliction classification applications from execution on startup of the wearable device, wherein each health affliction classification application of the set of health affliction classification applications remains idle unless and until execution thereof is initiated as part of the prioritized order of execution.

14. A computer program product comprising:
a non transistor y computer readable storage medium readable by a processing circuit and storing instructions for execution by the processing circuit for performing a method comprising:
controlling power consumption of a wearable device of a user by selectively starting and stopping, automatically by the processing circuit, execution of a set of health affliction classification applications on the wearable device of the user, the controlling comprising:
monitoring device notifications on at least one mobile device of the user for health affliction information, wherein the monitoring monitors notifications corresponding to various different electronic communication services, including text and e-mail messaging services, and wherein the monitoring is performed at least in part as the set of health affliction classification applications on the wearable device are idle;
invoking an analysis of one or more notifications of the monitored device notifications, the analysis comprising checking the monitored notifications for textual content informing of potential health afflictions and attempting to ascertain a health affliction and an afflicted individual having the health affliction; and
Initiating execution of the set of health affliction classification applications on the wearable device in a prioritized order of execution, based on the analyzing being initially unable to ascertain a health affliction after attempting to ascertain the health affliction;
wherein the initiating execution initiates execution of one or more health affliction classification applications of the set of health affliction classification applications in-series until a health affliction is identified, wherein, based on initiating execution of a health affliction classification application of the one or more health affliction classification applications, an attempt is made to identify the health affliction prior to initiating execution of a sequentially-next health affliction classification application of the one or more health affliction classification applications, wherein based on identifying the health affliction after initiating execution of a health affliction classification application, the initiating execution avoids initiating execution of any sequentially-next health affliction classification application of the one or more health affliction classification applications, and wherein the method further comprises logging an indication of the health affliction on the mobile device.

15. The computer program product of claim 14, wherein the method further comprises:
- based on the analyzing being initially unable to ascertain an afflicted individual having the health affliction, monitoring for intake of medicine by the user;
- identifying, based on content of the one or more notifications, one or more other users who may potentially be afflicted with the health affliction; and
- initiating monitoring, by one or more other devices of the one or more other users, for intake of medicine by the one or more other users.

16. The computer program product of claim 14, wherein the order of execution is prioritized based on at least one selected from the group consisting of: location of the user, weather of the location of the user, time of year, and a medical history of the user.

17. The computer program product of claim 14, wherein the selectively starting and stopping execution of the set of health affliction classification applications comprises blocking the set of health affliction classification applications from execution on startup of the wearable device, wherein each health affliction classification application of the set of health affliction classification applications remains idle unless and until execution thereof is initiated as part of the prioritized order of execution.

* * * * *